US011944104B2

(12) United States Patent
Putseys et al.

(10) Patent No.: US 11,944,104 B2
(45) Date of Patent: Apr. 2, 2024

(54) VARIANT MALTOGENIC ALPHA-AMYLASE

(71) Applicant: DSM IP ASSETS B.V., Heerlen (NL)

(72) Inventors: Joke Anneleen Putseys, Echt (NL); Aloysius Wilhelmus Rudolphus Hubertus Teunissen, Echt (NL); René Marcel De Jong, Echt (NL); Jeroen Godefrooij, Echt (NL); Helma Arina Stolze-Lagerweij, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 776 days.

(21) Appl. No.: 17/045,062

(22) PCT Filed: Apr. 4, 2019

(86) PCT No.: PCT/EP2019/058523
§ 371 (c)(1),
(2) Date: Oct. 2, 2020

(87) PCT Pub. No.: WO2019/193102
PCT Pub. Date: Oct. 10, 2019

(65) Prior Publication Data
US 2021/0161158 A1  Jun. 3, 2021

(30) Foreign Application Priority Data
Apr. 5, 2018  (EP) .................................... 18165871

(51) Int. Cl.
*C12N 9/26* (2006.01)
*A21D 8/04* (2006.01)
(52) U.S. Cl.
CPC ........... *A21D 8/042* (2013.01); *C12N 9/2414* (2013.01); *C12Y 302/01133* (2013.01)
(58) Field of Classification Search
CPC .... A21D 8/042; C12N 9/2414; C12N 9/2417; C12Y 302/01133
See application file for complete search history.

(56) References Cited

U.S. PATENT DOCUMENTS 9,301,533 B2 * 4/2016 De Jong .............. C12N 9/2417
10,327,449 B2   6/2019 De Jong et al.

FOREIGN PATENT DOCUMENTS

| EP | 2486799 A1 | 8/2012 |
| WO | 99/43794 A1 | 9/1999 |
| WO | 2006/032281 A2 | 3/2006 |
| WO | 2007094391 A1 | 7/2009 |
| WO | 2014/131842 A1 | 9/2014 |

OTHER PUBLICATIONS

International Search Report Issued in Counterpart Application No. PCT/EP2019/058523, dated May 17, 2019.
Database Geneseq [Online], Dec. 28, 2007, "Thermococcus sp. B1001 cyclodextrin glycosyltransferase, SEQ ID No. 12", XP002781360, retrieved from EBI accession No. GSP: ALT01687.

* cited by examiner

Primary Examiner — Nikki H. Dees
Assistant Examiner — Andrew E Merriam
(74) Attorney, Agent, or Firm — McBee Moore & Vanik IP, LLC

(57) ABSTRACT

The present invention relates to a variant polypeptide having maltogenic alpha-amylase activity wherein the polypeptide comprises an amino acid sequence, which, when aligned with an amino acid sequence of SEQ ID NO: 1, comprises an amino acid substitution F188L/I, S200N, and D261G, and optionally a further amino acid substitution T288P, wherein the amino acid substitutions are determined with reference to SEQ ID NO: 1, and wherein the polypeptide has an amino acid sequence which has at least 70%, 75%, 80%, 85%, 90%, 95%, 96%, 97%, 98%, or at least 99% identity to the amino acid sequence of SEQ ID NO: 1. The invention also relates to a process for the preparation of a dough or a baked product wherein the variant polypeptide is used.

19 Claims, No Drawings
Specification includes a Sequence Listing.

SEQUENCE LISTING

```
<160> NUMBER OF SEQ ID NOS: 5

<210> SEQ ID NO 1
<211> LENGTH: 686
<212> TYPE: PRT
<213> ORGANISM: Artificial Sequence
<220> FEATURE:
<223> OTHER INFORMATION: mature polypeptide of maltogenic alpha amylase
      derived from Bacillus stearothermophilus

<400> SEQUENCE: 1

Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
    130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175
```

```
Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
        195                 200                 205

Tyr Leu Thr Asp Ala Ala Val Gln Leu Val Ala His Gly Ala Asp Gly
        210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
                260                 265                 270

Tyr Ala Asn Asn Ser Gly Val Asn Val Leu Asp Phe Asp Leu Asn Thr
                275                 280                 285

Val Ile Arg Asn Val Phe Gly Thr Phe Thr Gln Thr Met Tyr Asp Leu
                290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
                340                 345                 350

Ser Arg Gly Thr Pro Ser Ile Tyr Tyr Gly Thr Glu Gln Tyr Met Ala
                355                 360                 365

Gly Gly Asn Asp Pro Tyr Asn Arg Gly Met Met Pro Ala Phe Asp Thr
                370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
                405                 410                 415

Asn Asp Val Tyr Ile Tyr Glu Arg Lys Phe Phe Asn Asp Val Val Leu
                420                 425                 430

Val Ala Ile Asn Arg Asn Thr Gln Ser Ser Tyr Ser Ile Ser Gly Leu
                435                 440                 445

Gln Thr Ala Leu Pro Asn Gly Ser Tyr Ala Asp Tyr Leu Ser Gly Leu
450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
                500                 505                 510

Asn Val Val Thr Ile Asp Gly Lys Gly Phe Gly Thr Thr Gln Gly Thr
                515                 520                 525

Val Thr Phe Gly Gly Val Thr Ala Thr Val Lys Ser Trp Thr Ser Asn
                530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
                580                 585                 590

Pro Thr Asn Leu Gly Asp Lys Ile Tyr Leu Thr Gly Asn Ile Pro Glu
```

```
                595               600               605
Leu Gly Asn Trp Ser Thr Asp Thr Ser Gly Ala Val Asn Asn Ala Gln
        610               615               620
Gly Pro Leu Leu Ala Pro Asn Tyr Pro Asp Trp Phe Tyr Val Phe Ser
625               630               635               640
Val Pro Ala Gly Lys Thr Ile Gln Phe Lys Phe Ile Lys Arg Ala
                645               650               655
Asp Gly Thr Ile Gln Trp Glu Asn Gly Ser Asn His Val Ala Thr Thr
        660               665               670
Pro Thr Gly Ala Thr Gly Asn Ile Thr Val Thr Trp Gln Asn
        675               680               685

<210> SEQ ID NO 2
<211> LENGTH: 2186
<212> TYPE: DNA
<213> ORGANISM: Artificial Sequence
<220> FEATURE:
<223> OTHER INFORMATION: ROM 1 module encoding a maltogenic alpha-
      amylase containing amino acid substitutions F188L, S200N, D261G
      and T288P

<400> SEQUENCE: 2
agcgcgtctc ctatgaaaaa gaaaacgctt tctttgttcg taggcctgat gctgctgatc      60
ggtttgctgt tctctggttc tcttccatac aacccaaacg ctgctgaagc aagctcaagt     120
gcttctgtaa aaggcgatgt gatttaccaa atcatcatcg accgtttcta tgacggagac     180
actactaaca caaacccagc aaaatcatac ggtctttacg atccgacaaa atcaaaatgg     240
aaaatgtact ggggcggaga tcttgaaggc gttcgtcaaa acttcctta cctgaaacaa     300 ttaggtgtga cgacgatttg gctgtctcct gttcttgata accttgatac attggcaggt     360
actgacaaca ctggctacca cggctactgg acgagagact tcaaacaaat cgaagaacac     420
ttcggaaact ggacgacatt cgatacgctt gtgaacgatg ctcaccaaaa cggaatcaaa     480
gttatcgttg atttcgttcc aaaccacagc actccattca agctaacga ttcaacgttc     540 gctgaaggcg tgctctttta caacaacgga acttacatgg caactacttt tgatgatgca     600
acaaaaggct acttccacca aacggagat atttctaact gggatgaccg ttatgaagct     660
caatggaaaa acctgactga tccggcaggc ttcagccttg ctgatcttaa ccaagaaaac     720
ggaacgattg ctcaatacct gacagacgct gctgttcaat tagttgctca cggtgcagac     780
ggacttcgca ttgacgctgt aaaacacttc aacagcggct ctctcaaaatc acttgctgac     840 aaactttacc aaaagaaaga tattttcctt gttggtgaat ggtacggaga tggcccaggt     900
actgcaaacc accttgaaaa agttcgttac gcaaacaaca gcggagtaaa cgtgcttgat     960
ttcgatttaa acccagtgat ccgtaatgta ttcggaacat tcactcaaac gatgtacgat    1020
ttgaacaaca tggtgaacca acaggaaat gaatacaaat acaagaaaaa cctgattaca    1080
ttcatcgaca accatgatat gtctcgtttt cttctgtaa acagcaacaa gcaaaccttg    1140
caccaagctc ttgcattcat tttaacttct cgcggaactc caagcattta ctacggaact    1200
gaacaataca tggcaggcgg aaatgatcct tacaaccgcg gaatgatgcc tgctttcgac    1260
acaacaacta ctgcattcaa agaagtatca acgcttgctg gtctaagacg caacaacgct    1320
gctattcaat acggaactac tactcaacgc tggatcaaca cgacgtttat catctacgaa    1380
cgcaaattct tcaacgatgt tgtgcttgtt gcaatcaacc gtaatacaca atcttcttac    1440
agcatttctg gtcttcaaac ggctcttcct aacggttctt acgctgatta cctaagcgga    1500
```

```
cttcttggcg aaacggcat ttctgtttca acggttctg ttgcttcttt cacacttgct    1560
cctggtgctg tttctgtttg gcaatactct acttctgctt ctgctcctca aatcggttct    1620
gtagctccaa acatgggcat cccaggaaac gttgtgacga ttgacggaaa aggcttcgga    1680
acaactcaag gtactgtaac gttcggcggc gttactgcaa ctgtaaaaag ctggacttct    1740
aaccgtatcg aagtgtacgt gccgaacatg gctgctggtt tgactgatgt gaaagtaact    1800
gcaggcggcg tttcttcaaa cctttacagc tacaacatcc tttctggtac tcaaacttct    1860
gttgtgttta ctgtgaaatc agctccgccg acaaaccttg gtgataaaat ctacctgact    1920
ggaaacatcc cagagcttgg caactggagc actgatacaa gcggcgctgt taacaacgct    1980
caaggaccgc ttcttgctcc aaactaccct gactggttct acgtattctc tgttcctgct    2040
ggaaaaacaa tccaattcaa attctttatc aaacgtgctg acggcacgat tcaatgggaa    2100
aacggttcaa accatgtggc aacaactcca actggtgcaa ctggtaacat cactgttact    2160
tggcaaaact aataaggaga cgcgct                                         2186

<210> SEQ ID NO 3
<211> LENGTH: 283
<212> TYPE: DNA
<213> ORGANISM: Artificial Sequence
<220> FEATURE:
<223> OTHER INFORMATION: BsmBI site

<400> SEQUENCE: 3
agcgcgtctc cccgctaaaa attttacaaa aaggtattga ctttccctac agggtgtgta    60
ataatttaat tataaggaca aatgaataaa gattgtatcc ttcggggcag ggtggaaatc    120
ccgaccggcg gtagtaaagc acatttgctt tagagtccgt gacccgtgtg cataagcacg    180
cggtggattc agtttaagct gaagccgaca gtgaaagtct ggatgggaga aggatggacg    240
gtaaataaca aagaaagga ggtgatcata tgggagacgc gct                       283

<210> SEQ ID NO 4
<211> LENGTH: 30
<212> TYPE: PRT
<213> ORGANISM: Artificial Sequence
<220> FEATURE:
<223> OTHER INFORMATION: forward primer

<400> SEQUENCE: 4

Cys Ala Ala Ala Cys Ala Thr Ala Thr Ala Gly Ala Gly Cys Thr Thr
1               5                   10                  15
Cys Cys Ala Gly Ala Thr Gly Ala Thr Gly Gly Cys Ala Gly
            20                  25                  30

<210> SEQ ID NO 5
<211> LENGTH: 27
<212> TYPE: DNA
<213> ORGANISM: Artificial Sequence
<220> FEATURE:
<223> OTHER INFORMATION: Reverse primer

<400> SEQUENCE: 5
ggtcatccca gttagaaata tctccgt                                        27
```

VARIANT MALTOGENIC ALPHA-AMYLASE

CROSS-REFERENCE TO RELATED APPLICATIONS

This application is the National Stage entry of International Application No. PCT/EP2019/058523, filed 4 Apr. 2019, which claims priority to European Patent Application No. 18165871.7, filed 5 Apr. 2018.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-536000_ST25.txt" created on 27 Aug. 2020, and 10,461 bytes in size) is submitted concurrently with the instant application, and the entire contents of the Sequence Listing are incorporated herein by reference.

BACKGROUND

Field

The present invention relates to a variant polypeptide having maltogenic alpha-amylase activity, a process for producing the maltogenic alpha-amylase, a premix or a dough comprising the maltogenic alpha-amylase and a process for the preparation of a dough or a baked product wherein a maltogenic alpha-amylase is used.

DESCRIPTION OF RELATED ART

Maltogenic alpha-amylases (glucan 1,4-α-maltohydrolase E.C. 3.2.1.133) are widely used in the baking industry as an anti-staling agent due to their ability to reduce retrogradation of starch.

WO99/43794 discloses variants of a maltogenic alpha-amylase, wherein the variants have different physicochemical properties such as an altered pH optimum or improved thermostability. WO/9943794 further discloses that the maltogenic alpha-amylase comprises three calcium ions in the protein structure. Since calcium is essential for maltogenic alpha-amylase activity of the enzyme, differences in calcium concentrations during its use in for instance baking processes may influence the performance of the maltogenic alpha-amylase enzyme.

WO2006/032281 discloses a process for preparing a dough or a dough-based product having a sucrose content of at least 10% by weight, using a variant maltogenic alpha-amylase with an improved sucrose tolerance.

WO2014/131842 discloses variants of polypeptides having alpha-amylase activity wherein the variants have an altered sucrose tolerance or an altered thermostability at different pH values.

There is a need for further polypeptides having maltogenic alpha-amylase activity which are less sensitive towards calcium concentrations for their performance.

SUMMARY

The present invention relates to a polypeptide having maltogenic alpha-amylase activity wherein the polypeptide comprises an amino acid sequence, which, when aligned with an amino acid sequence of SEQ ID NO: 1, comprises an amino acid substitution F188L/I, S200N, and D261G, and optionally a further amino acid substitution T288P, wherein the amino acid substitutions are determined with reference to SEQ ID NO: 1, and wherein the polypeptide comprises an amino acid sequence which has at least 70%, 75%, 80%, 85%, 90%, 95%, 96%, 97%, 98%, or at least 99% identity to the amino acid sequence according to SEQ ID NO: 1.

For instance, a polypeptide as disclosed herein is a polypeptide having maltogenic alpha-amylase activity, wherein the polypeptide has at least 40% residual maltogenic alpha-amylase activity after incubating the polypeptide in 50 mM malic acid buffer pH 5.2, containing 50 mM NaCl and 0.05% BSA and 2 mM EDTA at a temperature of 87.4° C. for 10 min. The residual maltogenic alpha-amylase activity is the residual maltogenic alpha-amylase activity as compared to the maltogenic alpha-amylase activity before said incubating, i.e. incubating the polypeptide in 50 mM malic acid buffer pH 5.2, containing 50 mM NaCl and 0.05% BSA and 2 mM EDTA at a temperature of 87.4° C. for 10 min.

Surprisingly, it was found that a variant polypeptide comprising an amino acid substitution F188L/I, S200N, and D261G, and optionally a further amino acid substitution T288P has a decreased dependency on calcium ions for thermostability as compared to a reference polypeptide. This was found advantageous since $Ca^{2+}$ concentrations can vary in processes for preparing a baked product due to differences in hardness (calcium concentration) of local water and other ingredients used for the preparation of a baked product which may or may not contain calcium ions. A reference polypeptide as disclosed herein may be a polypeptide not comprising amino acid substitution F188L/I, S200N, and D261G and optionally a further amino acid substitution T288P, which are determined with reference to SEQ ID NO:1. A reference polypeptide may be a polypeptide comprising or containing SEQ ID NO: 1. A reference polypeptide may be a polypeptide having maltogenic alpha-amylase activity comprising or containing SEQ ID NO: 1 which may comprise amino acid substitutions F188L, D261G and/or T288P. A decreased dependency on calcium ions for thermostability of a polypeptide having maltogenic alpha-amylase activity was found advantageous in baking applications since water used for preparing baked products can have different concentrations of calcium ions depending on the origin of the water and the location where a baked product is prepared.

It was further found that bread prepared with a polypeptide having maltogenic alpha-amylase activity as disclosed herein exhibited improved properties such a reduced crumb firmness and/or a reduced decrease and/or more stable crumb resilience as compared to bread prepared with a reference polypeptide.

The invention further relates to a recombinant host cell comprising a nucleic acid sequence encoding a variant polypeptide according to the present invention and a method for the preparation of a polypeptide as disclosed herein comprising cultivating a host cell in a suitable fermentation medium, under conditions that allow expression of the polypeptide, and preparing the polypeptide, and optionally recovering the polypeptide.

The invention further relates to the use of a variant polypeptide of the present invention, or a composition comprising a polypeptide according to the present invention in the preparation of a premix, dough, or a baked product.

Also disclosed is a premix comprising flour and a polypeptide as disclosed herein.

The present invention also relates to a dough comprising a polypeptide according to the present invention or a composition, or a premix as disclosed herein, and a method for preparing a dough comprising adding a polypeptide as disclosed herein to the dough.

The present invention also relates to a process for the preparation of a baked product comprising baking the dough comprising the polypeptide as disclosed herein.

DEFINITIONS

The term 'baked product' refers to a baked food product prepared from a dough.

Examples of baked products, whether of a white, brown or whole-grain type, include bread, typically in the form of loaves or rolls, French baguette-type bread, pastries, croissants, brioche, panettone, pasta, noodles (boiled or (stir-) fried), pita bread and other flat breads, tortillas, tacos, cakes, pancakes, cookies in particular biscuits, doughnuts, including yeasted doughnuts, bagels, pie crusts, steamed bread, crisp bread, brownies, sheet cakes, snack foods (e.g., pretzels, tortilla chips, fabricated snacks, fabricated potato crisps).

The term "dough" is defined herein as a mixture of flour and other ingredients. Usually, dough is firm enough to knead or roll. The dough may be fresh, frozen, prepared or parbaked. Dough is usually made from basic dough ingredients including (cereal) flour, such as wheat flour or rice flour, water and optionally salt. For leavened products, primarily baker's yeast is used, and optionally chemical leavening compounds can be used, such as a combination of an acid (generating compound) and bicarbonate. Cereals from which flour can be made include maize, rice, wheat, barley, sorghum, millet, oats, rye, triticale, buckwheat, quinoa, spelt, einkorn, emmer, durum and kamut. The term dough herein also includes a batter. A batter is a semi-liquid mixture, being thin enough to drop or pour from a spoon, of one or more flours combined with liquids such as water, milk or eggs used to prepare various foods, including cake.

The term "pre-mix" is defined herein to be understood in its conventional meaning, i.e. as a mix of baking agents, generally including flour, which may be used not only in industrial bread-baking plants/facilities, but also in retail bakeries. The pre-mix may be prepared by mixing the polypeptide having maltogenic alpha-amylase activity or the enzyme composition as disclosed herein with ingredients such as flour, starch or a salt.

The term "control sequence" as used herein refers to components involved in the regulation of the expression of a coding sequence in a specific organism or in vitro. Examples of control sequences are transcription initiation sequences, termination sequences, promoters, leaders, signal peptides, propeptides, prepropeptides, or enhancer sequences; Shine-Delgarno sequences, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion.

As used herein, the term "endogenous" refers to a nucleic acid or amino acid sequence naturally occurring in a host.

The term "expression" includes any step involved in the production of the polypeptide including, but not limited to, transcription, post transcriptional modification, translation, post-translational modification, and secretion.

An expression vector comprises a polynucleotide coding for a polypeptide, operably linked to the appropriate control sequences (such as a promoter, and transcriptional and translational stop signals) for expression and/or translation in vitro. The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector, which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon. Vectors preferred for use in bacteria are for example disclosed in WO-A1-2004/074468.

A host cell as defined herein is an organism suitable for genetic manipulation and one which may be cultured at cell densities useful for industrial production of a target product, such as a polypeptide according to the present invention. A host cell may be a host cell found in nature or a host cell derived from a parent host cell after genetic manipulation or classical mutagenesis. Advantageously, a host cell is a recombinant host cell. A host cell may be a prokaryotic, archaebacterial or eukaryotic host cell. A prokaryotic host cell may be, but is not limited to, a bacterial host cell. A eukaryotic host cell may be, but is not limited to, a yeast, a fungus, an amoeba, an algae, a plant, an animal, or an insect host cell.

A nucleic acid or polynucleotide sequence is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein. A nucleic acid or polynucleotide sequence is defined herein as a nucleotide polymer comprising at least 5 nucleotide or nucleic acid units. A nucleotide or nucleic acid refers to RNA and DNA.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in the presence of a specific substrate under certain conditions may be referred to as enzymes. It will be understood that, because of the degeneracy of the genetic code, a multitude of nucleotide sequences encoding a given polypeptide may be produced.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 80% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

A "mature polypeptide" is defined herein as a polypeptide in its final form and is obtained after translation of a mRNA into polypeptide and post-translational modifications of said polypeptide. Post-translational modifications include N-terminal processing, C-terminal truncation, glycosylation, phosphorylation and removal of leader sequences such as signal peptides, propeptides and/or prepropeptides by cleavage. A polypeptide according to SEQ ID NO: 1, such as polypeptide comprising amino acids 1 to 686 of SEQ ID NO: 1, is a mature polypeptide.

A "mature polypeptide coding sequence" means a polynucleotide that encodes a mature polypeptide.

The term "promoter" is defined herein as a DNA sequence that binds RNA polymerase and directs the polymerase to the correct downstream transcriptional start site of a nucleic acid sequence to initiate transcription. Suitable bacterial promotors are for instance disclosed in in WO-A1-2004/074468.

The term "recombinant" when used with reference to a nucleic acid or protein indicates that the nucleic acid or protein has been modified in its sequence if compared to its native form by human intervention. The term "recombinant" when referring to a cell, such as a host cell, indicates that the genome of the cell has been modified in its sequence if compared to its native form by human intervention. The term "recombinant" is synonymous with "genetically modified".

Sequence identity, or sequence homology are used interchangeable herein. To determine the percentage of sequence homology or sequence identity of two amino acid sequences or of two nucleic acid sequences, the sequences are aligned for optimal comparison purposes. To optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms. After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http://www.ncbi.nlm.nih.gov/.

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. The codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 2, but still encoding the polypeptide according to the invention.

As used herein, the terms "variant" or "mutant" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination

DETAILED DESCRIPTION

The present invention relates to a variant polypeptide having maltogenic alpha-amylase activity wherein the polypeptide comprises an amino acid sequence, which, when aligned with an amino acid sequence of SEQ ID NO: 1, comprises or contains an amino acid substitution F188L/I, S200N, and D261G, and optionally a further amino acid substitution T288P, wherein the amino acid substitutions are determined with reference to SEQ ID NO: 1, and wherein the polypeptide comprises an amino acid sequence which has at least 70%, 75%, 80%, 85%, 90%, 95%, 96%, 97%, 98%, or at least 99% identity to the amino acid sequence according to SEQ ID NO: 1. A variant polypeptide as disclosed herein may be an isolated, pure or synthetic variant polypeptide.

A polypeptide as disclosed herein may be a polypeptide having maltogenic alpha-amylase activity, wherein the polypeptide has at least 40% residual maltogenic alpha-amylase activity after incubating the polypeptide in 50 mM malic acid buffer pH 5.2, containing 50 mM NaCl and 0.05% BSA and 2 mM EDTA at a temperature of 87.4° C. for 10 min as compared to the maltogenic alpha-amylase activity before heat treatment. Preferably, a polypeptide having maltogenic alpha-amylase activity as disclosed herein is a polypeptide which has at least 45%, 50%, 55%, or at least 60% residual maltogenic alpha-amylase activity after incubating the polypeptide in 50 mM malic acid buffer pH 5.2, containing 50 mM NaCl and 0.05% BSA and 2 mM EDTA at a temperature of 87.4° C. for 10 min as compared to the maltogenic alpha-amylase activity before heat treatment. The polypeptide having maltogenic alpha-amylase activity as disclosed herein may be a variant polypeptide as disclosed herein.

Surprisingly it was found that a polypeptide having maltogenic alpha-amylase activity as disclosed herein has a decreased dependency on calcium ions for thermostability as compared to a reference polypeptide.

In one embodiment a variant polypeptide having maltogenic alpha-amylase activity is a polypeptide, wherein the polypeptide comprises an amino acid sequence, which, when aligned with an amino acid sequence of SEQ ID NO: 1, comprises an amino acid substitution F188L, S200N, D261G, and T288P, wherein the amino acid substitutions are determined with reference to SEQ ID NO: 1.

Surprisingly, it was found that the maltogenic alpha-amylase activity of a polypeptide as disclosed herein has a decreased dependency on calcium ions for thermostability as compared to a reference polypeptide.

Dependency on calcium ions for thermostability as used herein may be determined by measuring the residual maltogenic alpha-amylase activity of a polypeptide having maltogenic alpha-amylase activity as disclosed herein after incubating the polypeptide at a temperature of from 70° C. to 95° C., such as from 75° C. to 90° C., such as from 77° C. to 89° C. for 10 minutes, in the presence of EDTA, for instance in the presence of 2 mM or 10 mM of EDTA. The residual activity of a variant polypeptide as disclosed herein is compared to the residual activity of a reference polypeptide to determine decreased dependency.

Dependency on calcium ions for thermostability of a polypeptide having maltogenic alpha-amylase activity may also be determined by determining crumb firmness of a bread that has been prepared with a polypeptide having maltogenic alpha-amylase activity using water with different concentrations of calcium. The crumb firmness of a bread prepared with a variant polypeptide as disclosed herein is compared to the crumb firmness of a bread prepared with a reference polypeptide to determine the relative dependency, such as decreased dependency.

A reference polypeptide as disclosed herein may be a polypeptide not comprising amino acid substitution F188L/I, S200N, and D261G and optionally a further amino acid substitution T288P, which are determined with reference to SEQ ID NO:1. A reference polypeptide may be a polypeptide comprising SEQ ID NO: 1, or a polypeptide comprising SEQ ID NO: 1 and comprising amino acid substitution F188L, D261G and T288P, wherein the amino acid substitutions are defined with reference to SEQ ID NO: 1.

A polypeptide as disclosed herein may be a variant polypeptide having maltogenic alpha-amylase activity, wherein the polypeptide comprises an amino acid sequence, which, when aligned with an amino acid sequence of SEQ ID NO: 1, comprises an amino acid substitution F188L/I, S200N, and D261G, and optionally a further amino acid substitution T288P, wherein the amino acid substitutions are determined with reference to SEQ ID NO: 1, wherein the variant polypeptide has a decreased dependency on calcium ions for thermostability as compared to a reference polypeptide not having the amino acid substitutions F188L/I, S200N, and D261G, and optionally a further amino acid substitution T288P.

A variant polypeptide as disclosed herein may comprise further substitutions, deletions and/or insertions at one or more further amino acid positions. For instance, a polypeptide having maltogenic alpha-amylase activity as disclosed herein may comprise 1, 2, 3, 4, 5, 6, 7, 8, 9, 10, 11 or 12 or more further amino substitutions, deletions and/or insertions, whereby the polypeptide still has the activity or function of the polypeptide as disclosed herein.

In one embodiment a variant polypeptide comprising the amino acid substitutions F188L/I, S200N, and D261G, and optionally a further amino acid substitution T288P as disclosed herein comprises an amino acid sequence which has at least 70%, 75%, 80%, 85%, 90%, 95%, 96%, 97%, 98%, or at least 99% identity to the amino acid sequence according to SEQ ID NO: 1. A polypeptide as disclosed herein may be a synthetic polypeptide. A polypeptide as disclosed herein is a mature polypeptide.

The amino acids are referred herein with their single letter code known to a person skilled in the art and can be found in Sambrook & Russell, *Molecular Cloning: A Laboratory Manual*, 3rd Ed., CSHL Press, Cold Spring Harbor, NY, 2001. To exemplify, the amino acids at the positions identified herein F188L/I, S200N, D261G and T288P in their three-letter code and full name are: F=Phe=phenylalanine, L=Leu=Leucine; 1=Ile=Isoleucine; S=Ser=Serine; N=Asn=Asparagine; D=Asp=Aspartic Acid; G=Gly=Glycine; T=Thr=Threonine; P=Pro=Proline.

A polypeptide having maltogenic alpha-amylase activity as disclosed herein is a maltogenic alpha-amylase enzyme classified as EC 3.2.1.133. An example of a maltogenic alpha-amylase is for instance disclosed in WO91/04669.

Also disclosed herein is a composition comprising a polypeptide as disclosed herein. A composition as disclosed herein, may comprise a carrier, an excipient, an auxiliary enzyme, or other compounds. Typically, a composition, or a formulation, comprises a compound with which a variant polypeptide having maltogenic alpha-amylase activity may be formulated. An excipient as used herein is an inactive substance formulated alongside with a polypeptide as disclosed herein, for instance milk powder, gluten, sucrose or lactose, glycerol, sorbitol, ascorbic acid, flavours or salts such as sodium chloride. An auxiliary enzyme in a composition comprising a polypeptide as disclosed herein may for instance be an alpha-amylase, a beta-amylase, a protease, a lipase, such as a phospholipase, a glucose oxidase, amyloglucosidase and/or a hemicellulase such as xylanase.

A composition comprising a polypeptide as disclosed herein may be a liquid composition or a solid composition. A liquid composition usually comprises water. When formulated as a liquid composition, the composition usually comprises components that lower the water activity, such as glycerol, sorbitol or sodium chloride (NaCl). A solid composition comprising a polypeptide as disclosed herein may comprise a granulate comprising the enzyme or the composition comprises an encapsulated polypeptide in liquid matrices like liposomes or gels like alginate or carrageenan.

A process for preparing a composition comprising a polypeptide as disclosed herein may comprise spray drying a fermentation medium comprising the polypeptide, or granulating, or encapsulating a polypeptide as disclosed herein, and preparing the composition. There are many techniques known in the art to encapsulate or granulate a polypeptide or enzyme (see for instance G. M. H. Meesters, "Encapsulation of Enzymes and Peptides", Chapter 9, in N. J. Zuidam and V. A. Nedović (eds.) "Encapsulation Technologies for Active Food Ingredients and food processing" 2010).

In one aspect, a nucleic acid sequence encoding a variant polypeptide according to the present invention is disclosed. A nucleic acid as disclosed herein may be an isolated, pure, recombinant, synthetic or variant nucleic acid of the nucleic acid of SEQ ID NO: 2. A variant nucleic acid sequence may for instance have at least 70%, 80%, 85%, 90%, 95%, or 96%, 97%, 98% or 99% sequence identity to SEQ ID NO:2 or may comprise SEQ ID NO: 2.

Also disclosed herein is an expression vector comprising a nucleic acid sequence as disclosed herein, operably linked to one or more control sequences that direct expression of the nucleic acid sequence.

There are several ways of inserting a nucleic acid into a nucleic acid construct or an expression vector which are known to a person skilled in the art, see for instance Sambrook & Russell, *Molecular Cloning: A Laboratory Manual*, 3rd Ed., CSHL Press, Cold Spring Harbor, NY, 2001. It may be desirable to manipulate a nucleic acid encoding a polypeptide of the present invention with control sequences, such as promoter and terminator sequences.

Also disclosed herein is a recombinant host cell comprising a nucleic acid sequence as disclosed herein, or an expression vector as disclosed herein.

A suitable recombinant host cell for expressing a polypeptide as disclosed herein include fungi such as *Aspergillus*, or *Trichoderma* sp., for instance *Aspergillus niger, A. oryzae, A. aculeatus,* or *T. reesei*, or yeasts such as *Saccharomyces* sp., *Kluyveromyces* sp. or *Pichia* sp., for instance *S. cereviseae. K. lactis, P. pastoris*, or bacteria such as *Escherichia coli* and *Bacillus* sp., for instance *B. subtilis, B. licheniformis, B. amyloliquefaciens.*

In one aspect disclosed herein is a method for the preparation of a polypeptide as disclosed herein, comprising cultivating a host cell as disclosed herein in a suitable fermentation medium under conditions that allow expression of the polypeptide, and preparing the polypeptide, and optionally recovering the polypeptide. A person skilled in the art knows how to perform a process for preparing a polypeptide having maltogenic alpha-amylase activity depending on the host cell used. A suitable fermentation medium usually comprises a carbon and a nitrogen source. Usually a fermentation medium may have a pH value of between 4 and 8. A suitable temperature at which a host cell is cultivated is usually between 20 and 60° C., for instance between 25 and 50° C.

Host cells can be cultivated in shake flasks, or in fermenters having a volume of 0.5 or 1 litre or larger up to 10 to 100 or more cubic metres. Cultivation may be performed aerobically or anaerobically depending on the requirements of a host cell.

Advantageously a polypeptide as disclosed herein is recovered or isolated from the fermentation medium. Recovering or isolating a polypeptide from a fermentation medium may for instance be performed by centrifugation, filtration, and/or ultrafiltration.

Also disclosed herein is the use of a variant polypeptide according to the present invention, or a composition as disclosed herein in the preparation of a premix, dough, or a baked product.

In one aspect, the present disclosure relates to the use of a variant polypeptide as disclosed herein or a composition as disclosed herein for reducing crumb firmness of bread. Reducing crumb firmness as used herein is defined as reducing the increase of crumb firmness, for instance upon storage of bread. It was found that crumb firmness of the bread prepared with a variant polypeptide as disclosed herein was less affected by the presence of calcium during the preparation of bread as compared to the crumb firmness of bread prepared with a reference polypeptide. The use of a variant polypeptide or the use of a composition as disclosed herein may further comprise reducing the decrease of crumb resilience of bread.

Accordingly, the present disclosure relates to a process for reducing the increase of crumb firmness and/or reducing decrease of crumb resilience of bread comprising using a variant polypeptide as disclosed herein during preparation of bread. Using a variant polypeptide as disclosed herein during preparation of bread usually comprises adding the variant polypeptide to a dough and baking the dough.

Reduced crumb firmness and/or reduced decrease of crumb resilience of bread was determined as compared to bread prepared with a reference polypeptide. Reduced crumb firmness and/or reduced decrease of crumb resilience is determined after storage of bread, for instance storage at room temperature for 1 to 21 days, for instance for 2 to 14 days, for instance for 3 to 7 days, for instance for 4 to 6 days. Reduced crumb firmness and/or reduced decrease of crumb resilience may also be determined after storage at a temperature of from 0° C. to 8° C. for instance from 1° C. to 6° C. for a period of from 1 to 10 days, for instance from 2 to 8 days, or from 3 to 7 days.

Also disclosed herein is a premix, which comprises flour and a variant polypeptide according to the present invention, or a composition as disclosed herein.

Also disclosed herein is a dough comprising a polypeptide according to the present invention, a composition as disclosed herein, or a premix as disclosed herein.

Also disclosed is a process for the preparation of a dough comprising adding a polypeptide according to the present invention, or a composition as disclosed herein, or a premix as disclosed herein to the dough. Processes for preparing a dough are commonly known the art.

The present disclosure also relates to a process for the preparation of a baked product comprising baking the dough as disclosed herein. A baked product may be any suitable baked product as defined herein above. Processes for baking a dough to prepare a bread are known to a person skilled in the art. A process for the preparation of a baked product comprises a step of making a dough, adding a polypeptide, a composition or a premix as disclosed herein to the dough and preparing the baked product. Surprisingly, it was found that a baked product such as bread prepared in a process as disclosed herein exhibited improved properties such as reduced increase of crumb firmness and/or reduced decrease of crumb resilience as compared to a bread prepared with a reference polypeptide as defined herein above.

EXAMPLES

Molecular Biology Techniques

Molecular biology techniques known to the skilled person are performed according to Sambrook & Russell, Molecular Cloning: A Laboratory Manual, 3rd Ed., CSHL Press, Cold Spring Harbor, NY, 2001. Polymerase chain reaction (PCR) is performed on a thermocycler with Phusion High-Fidelity DNA polymerase (Finnzymes O Y, Aspoo, Finland) according to the instructions of the manufacturer.

Materials & Methods

Enzymes

Bakezyme® MAM 10000 was commercially available at DSM.

Strains and Plasmids

Bacillus subtilis strain BS154 (CBS 363.94) (ΔaprE, ΔnprE, amyE-, spo-) is described in Quax and Broekhuizen 1994 Appl Microbiol Biotechnol. 41: 425-431.

The multipurpose integration expression vector pDBC1 is described in WO2015118126A1. Bacillus stearothermophilus (renamed Geobacillus stearothermophilus) C599 (NC/B 11873) is described in WO91/04669. The gene encoding the maltogenic alpha-amylase was synthetically made with mutations to encode modifications F188L, S200N, D261G and T288P (as compared to SEQ ID NO: 1) and at both ends a BsmBI site is attached making the ROM1 module (SEQ ID NO: 2).

Similarly, genes encoding wild-type maltogenic alpha-amylase (SEQ ID NO: 1) and maltogenic alpha-amylase with modifications F188L, S200N, and D261G, or F188L, D261G and T288P (as compared to SEQ ID NO: 1) were made The promoter PE4 (indicated herewith as P15 promoter) of the B. subtilis bacteriophage SP01 is described in Lee et al., 1980, Mol. Gen. Genet. 180: 57-65, and in Stewart C. R. et al (1998) Virology. 246(2): 329-340. The promoter is combined with the RSE (RK41_SWITCH deletion, EP2186880) and RBS S16. The fragment is made synthetically and at both ends a BsmBI site is attached (SEQ ID NO: 3).

DNA Constructs and Transformation

The final integration construct, containing the vector pDBC1, the P15 promoter module and the ROM1 module, were assembled using the StarGate type IIS restriction enzyme cloning system (IBA, GmbH, Gottingen, Germany) which was used according to the instructions of the manufacturer. The overhangs of the BsmBI site were chosen to avow only one assembly of the modules. The reaction mixture was used to transform Bacillus subtilis strain 135154. The transformants were selected in spectinomycin (100 g/ml) containing agar plates. The amyE 5' and 3' regions on pDBC1 targeted the constructs to the genomic amyE locus. The double cross over transformants were only spectinomycin resistant whereas the undesired single crossover transformants were also erythromycin resistant. In addition, the clones were checked by PCR using the following primer combination: a forward primer located at the 5' end of the amyE locus (just outside the flanking sequence present in pDBC1) (SEQ ID NO: 4) and a reverse primer located at the 5'end of the ROM1 module (SEQ ID NO: 5). In the correct clones a fragment of 990 nt is amplified.

Expression of Maltogenic Alpha-Amylase Variants in Shake Flasks

The Bacillus subtilis strains harboring the ROM1 module were placed on 2*TY agar plates and grown for 24 hours at 37° C. A pre-culture of 20 ml 2*TY medium composed of 1.6% (w/v) Bacto tryptone, 1% (w/v) Yeast extract and 0.5% (w/v) NaCl in 100 ml Erlenmeyer flasks were inoculated with the B. subtilis cells taken from the plates. The cultures were shaken vigorously at 37° C. and 250 rpm for 16 hours and 0.2 ml culture medium was used to inoculate 20 ml SMM medium. SMM pre-medium contained 1.25% (w/w) yeast extract, 0.05% (w/w) $CaCl_2$), 0.075% (w/w) $MgCl_2.6H_2O$, 15 µg/l $MnSO_4.4H_2O$, 10 µg/l $CoCl_2.6H_2O$, 0.05% (w/w) citric acid, 0.025% (w/w) antifoam 86/013 (Basildon Chemicals, Abingdon, UK). To complete the SMM medium, 20 ml of 5% (w/v) maltose and 20 ml of a 200 mM Na-phosphate buffer stock solution (pH 6.8), both prepared and sterilized separately, were added to 60 ml SMM pre-medium. These cultures are incubated for 48 hours at 37° C. and 250 rpm. The supernatants were harvested and analyzed for enzyme activity. The maltogenic alpha-amylase activity of the variants is measured according to the assay as described in below.

Enzyme Activity Assays

Amylase activity was measured based on the ceralpha method as described by Megazyme (R-CAAR-4, Megazyme, Ireland). The method makes use of a non-reducing end blocked p-nitrophenyl maltoheptaoside substrate (BPNPG7). Appropriate enzyme dilutions were prepared in 50 mM malic acid buffer pH 5.2, containing 50 mM NaCl, 2 mM $CaCl_2$) and 0.05% BSA (assay buffer). Of these dilutions, 10 µl was added to 90 µl of preheated ceralpha reagent (R-CAAR-4; dissolved in 10 ml MQ water and diluted to working solution with 8 ml of malic acid buffer) at 37° C. The incubation was stopped after 423 seconds by addition of 75 µl of a 170 mM Tris solution. The absorbance at 405 nm was recorded, 130 seconds after reaction termination. Sample blanks were measured by reversing the pipetting order: first stop reagent, then sample and substrate. Activity is calculated from the delta absorbance between sample and blank incubations. The assay was performed using a Konelab Arena 30 analyzer, set at 37° C. incubation temperature (Thermo).

One unit of activity is defined as the amount of enzyme releasing one nmol/s p-nitrophenol from the substrate under conditions of the test.

Crumb Firmness and Resilience

Crumb firmness (or hardness; both being the opposite of softness) and crumb resilience of bread slices were measured using the Texture Analyzer and were also evaluated empirically by the skilled test baker. To evaluate these crumb properties, breads were cut into slices with a thickness of 2.5 cm, and the firmness was measured using a Texture Analyzer TA-XT Plus (Stable MicroSystems), with the following settings: compression test mode, pre-test speed of 3 mm/s, test speed of 1 mm/s, distance of 5 mm, hold time of 10 s and trigger force of 5 g.

The crumb firmness is the maximum peak force during compression, recorded in gram.

The crumb resilience is the ratio of the force at the end of the 10 s hold time to the maximum force. Crumb resilience is expressed as percentage.

Example 1. Influence of EDTA on Thermostability of Maltogenic Alpha-Amylase Variants Thermostability of the maltogenic alpha-amylase wild type and variants produced above was assessed by incubating samples of the enzymes (0.1-0.3 mg/ml) in 50 mM malic acid buffer pH 5.2, containing 50 mM NaCl and 0.05% BSA, and 0, 2 mM or 10 mM EDTA in a PCR plate in a BioRad thermocycler at 87.4° C. for 10 min. After the 10 min incubations, the samples were cooled to 4° C.

Wild-type MAM exhibited only about 3% residual maltogenic alpha-amylase activity after treatment at 87.4° C. for 10 min in normal tap-water.

Therefore, the thermostability of the enzymes was also tested in a similar way at a temperature of 79° C. in the malic acid buffer as described above and containing 0 or 10 mM EDTA.

Maltogenic alpha-amylase activity in the samples was determined as described above before and after temperature treatment. The residual activity after temperature treatment was expressed as a percentage of the activity prior to temperature treatment.

The results in Table 1 and 1a and Table 2 and 2a show that the two MAM variants comprising the amino acid substitution S200N, i.e. MAM variant 1 (F188L, S200N, D261G, T288P) to and MAM variant 2 (F188L, S200N, D261G) were more thermostable compared to MAM variant 3 and wildtype (wt) MAM in the presence of EDTA. This indicates that the thermostability of MAM variant 1 and MAM variant 2 was more robust towards calcium-chelation by EDTA as compared to MAM variant 3 and wildtype MAM.

TABLE 1

Residual maltogenic alpha-amylase activity after treatment at 87.4° C. for 10 min in the absence and presence of EDTA

| Variant | Substitutions compared to SEQ ID NO: 1 | 0 mM EDTA | 2 mM EDTA | 10 mM EDTA |
|---|---|---|---|---|
| 1 | F188L, S200N, D261G, T288P | 83% | 64% | 6% |
| 2 | F188L, S200N, D261G | 66% | 51% | 6% |
| 3 | F188L, D261G, T288P | 78% | 39% | 0% |

TABLE 2

Residual maltogenic alpha-amylase activity after treatment at 79° C. for 10 minutes in the absence and presence of EDTA

| Variant | Substitutions compared to SEQ ID NO: 1 | 0 mM EDTA | 10 mM EDTA |
|---|---|---|---|
| 1 | F188L, S200N, D261G, T288P | 93% | 90% |
| 2 | F188L, S200N, D261G | 89% | 86% |
| 3 | F188L, D261G, T288P | 92% | 85% |
|   | Wild type | 81% | 72% |

The results in Table 1 and Table 2 are presented in Table 1a and Table 2a as the relative residual activity of each variant in the presence of EDTA, expressed as a percentage of the residual activity for that variant measured in the absence of EDTA.

TABLE 1a

Relative residual maltogenic alpha-amylase activity after treatment at 87.4° C. for 10 min in the presence of EDTA, expressed as a percentage of the residual activity after treatment in the absence of EDTA

| Variant | Substitutions compared to SEQ ID NO: 1 | 0 mM EDTA | 2 mM EDTA | 10 mM EDTA |
|---|---|---|---|---|
| 1 | F188L, S200N, D261G, T288P | 100% | 77% | 7% |
| 2 | F188L, S200N, D261G | 100% | 77% | 9% |
| 3 | F188L, D261G, T288P | 100% | 50% | 0% |

TABLE 2a

Relative residual maltogenic alpha-amylase activity after treatment at 79° C. for 10 min in the presence of EDTA, expressed as a percentage of the residual activity after treatment in the absence of EDTA

| Variant | Substitutions compared to SEQ ID NO: 1 | 0 mM EDTA | 10 mM EDTA |
|---|---|---|---|
| 1 | F188L, S200N, D261G, T288P | 100% | 97% |
| 2 | F188L, S200N, D261G | 100% | 97% |
| 3 | F188L, D261G, T288P | 100% | 92% |
|   | Wild type | 100% | 89% |

Example 2. Influence of Calcium on the Performance of Maltogenic Alpha-Amylase in Baked Bread 2. 1. Baking of Bread White tin breads were baked according to a lean recipe (including 100% flour, 55-60% water, yeast, salt and basic bread improver (to improve dough handling in the bakery)) following the straight dough breadmaking procedure known to a person skilled in the art. This procedure involved a single mixing step after addition of all ingredients to the mixer, followed by fermentation, scaling and shaping, proofing and baking. The resulting breads were evaluated on crumb firmness after storage of the baked breads.

2.2. Ca-Dependency of Maltogenic Alpha-Amylase Performance in Bread

The crumb firmness of breads was determined in breads made from doughs with wild type maltogenic alpha-amylase (MAM) and variant MAM with the amino acid substitutions F188L, S200N, D261G, and T288P using water with different concentrations of calcium. Enzyme dosages of MAM and variant MAM were chosen such to reduce staling of bread to a similar degree as when 50 ppm Bakezyme® MAM 10000 was added.

MAM (Bakezyme® MAM 10000) (0.8 units/g flour) and variant MAM with the amino acid substitutions F188L, S200N, D261G, and T288P (0.1 units/g flour) were dosed in a bread recipe using water (2 mM Ca; corresponding to Ca levels in normal tap water), calcium-depleted water (demineralized water, 0 mM Ca) or calcium-enriched water (with a concentration of 10 mM Ca). Calcium ($CaCl_2.2H_2O$ (Merck)) was added to demineralized water to obtain water with 2 mM and 10 mM calcium. Breads were baked as described above. After baking, breads were stored at 6° C. for 7 days. Subsequently, the breads were brought to room temperature for 2 hr before being sliced and evaluated with respect to crumb firmness according to the method described above. Firmness of the bread crumb is an indication of staling of bread. The results in Table 3 show the firmness (%) of the bread crumb relative to the firmness of the bread crumb prepared with water containing 2 mM Ca.

The results in Table 3 show that the calcium concentration in water hardly affected the firmness of breads prepared with the MAM variant containing amino acid substitutions F188L, S200N, D261G, and T288P. In contrast, when no calcium was present in the water, the crumb firmness of breads prepared with the wild type MAM was much higher as compared to the crumb firmness of breads prepared with water wherein 2 or 10 mM of calcium was present. This indicates that the MAM variant depends less on calcium for its performance as anti-staling enzyme in bread.

TABLE 3

Crumb firmness (%) of breads after storage at 6° C. for 7 days of breads made with MAM or MAM variant 1 and water having 0, 2 or 10 mM of calcium.

| enzyme | 0 mM Ca | 2 mM Ca | 10 mM Ca |
|---|---|---|---|
| % Firmness after 7 days (relative to 2 mM Ca) MAM | 106% | 100% | 93% |
| MAM variant 1 | 101% | 100% | 98% |

Example 3. Effect of Variant and Wild-Type Maltogenic Alpha-Amylase on the Crumb Firmness and Crumb Resilience of White Tin Bread White tin breads were baked following the straight dough breadmaking procedure known to a person skilled in the art, using a recipe including 100% flour, 59% regular tap water, 2.4% yeast, 1.6% salt and basic concentrations of ascorbic acid and xylanases typically used to improve dough handling in the bakery. The percentages used in this recipe are baker's percentages, expressed relative to the amount of flour used (flour=100%). Wild type maltogenic alpha-amylase (MAM, 0.75 units/g flour) and variant MAM with the amino acid substitutions F188L, S200N, D261G, T288P (0.1 unit/g flour) were added to the flour.

The breadmaking procedure involved a single mixing step after addition of all ingredients to the mixer, followed by fermentation, scaling (to about 800 g doughs) and shaping, proofing and baking. After baking, breads were stored at ambient temperature for 7 days. Subsequently, the crumb firmness and the crumb resilience of the breads was determined as described above.

The results in Table 4 show that bread made with MAM variant 1 comprising the amino acid substitutions F188L, S200N, D261G, and T288P had a lower firmness and reduced decrease in resilience as compared to bread made with wild-type maltogenic amylase and compared to bread made without MAM (blank) after storage for 1, 4, or 7 days at ambient temperature.

TABLE 4

Firmness (g) and resilience (%) of the crumb of white breads made without maltogenic amylase (blank) or with wild-type MAM or MAM variant 1 comprising the amino acid substitutions F188L, S200N, D261G and T288P after storage at ambient temperature for several days.

| storage time (days) | Firmness (g) | | | Resilience (%) | | |
|---|---|---|---|---|---|---|
| | blank | MAM | MAM variant 1 | blank | MAM | MAM variant 1 |
| 1 | 346 | 351 | 288 | 74.0 | 72.7 | 74.2 |
| 4 | 657 | 452 | 363 | 68.7 | 72.3 | 73.5 |
| 7 | 849 | 538 | 416 | 66.1 | 69.9 | 73.0 |

Example 4. Effect of Variant Maltogenic Alpha-Amylases on the Quality of Whole Grain Bread Wholegrain breads were prepared according to a lean recipe (including 100% Acacia flour, 67% regular tap water, 2.4% yeast, 1.8% salt, 3% gluten-containing wholemeal bread improver, 0.25% DATEM, and 0.5% basic bread improver (with percentages expressed as baker's percentage, relative to the amount of flour=100%), following the straight dough breadmaking procedure known to a person skilled in the art. MAM variant 3 comprising amino acid substitutions F188L, D261G, T288P and MAM variant 1 comprising F188L, D261G, T288P and S200N were dosed at 0.1 units/g flour.

The breadmaking procedure involved a single mixing step after addition of all ingredients to the mixer, followed by fermentation, scaling and shaping, proofing and baking. After baking, the breads were stored at 6° C. for 5 days. Subsequently, the breads were brought to room temperature for 2 hours before being sliced and evaluated with respect to crumb firmness and resilience according to the method as described above.

The results in Table 4 show that the bread crumb of wholegrain breads prepared with MAM variant 1 comprising the amino acid substitutions F188L, D261G, T288P and S200N had a lower firmness (in g), and reduced decrease of resilience (in %) after storage at 6° C. up to 5 days as compared to the bread crumb of wholegrain breads prepared with MAM variant 3 comprising the amino acid substitutions F188L, D261G, and T288P.

TABLE 5

Crumb firmness (g) and resilience (%) of wholegrain breads made with MAM variant 3 comprising F188L, D261G, and T288P and MAM variant 1 comprising F188L, D261G, and T288P S200N after storage at 6° C. for several days.

| | Firmness (g) | | Resilience (%) | |
|---|---|---|---|---|
| Storage time (days) | Variant 3 | Variant 1 | Variant 3 | Variant 1 |
| 1 | 320 | 241 | 71.2 | 72.8 |
| 2 | 476 | 295 | 66.9 | 70.4 |
| 5 | 536 | 387 | 64.2 | 67.8 |

The breads were also evaluated sensorically by trained panellists, by scoring the bread crumbs on hardness (is the same as firmness, both being the inverse of softness), moistness, cohesiveness and crumbliness after a storage period at 6° C. for 5 days. The score indicates the average of all participants. Scores ranged from 1 to 9, with 1 being a very low (or absent) and 9 being very a high value of each of the characteristics. For hardness and crumbliness, a low score is considered positive, whereas for moistness and cohesiveness a high score is desirable to the consumer.

The results in Table 6 show that the breads made with MAM variant 1 comprising amino acid substitutions F188L, D261G, T288P and S200N resulted in better scores on hardness, moistness, cohesiveness and crumbliness than breads prepared with MAM variant 3 comprising amino acid substitutions F188L, D261G, and T288P.

TABLE 6

Sensory scores, given as average of all panellists, of 5-day old wholegrain breads baked with maltogenic alpha-amylase variant 1: F188L, D261G, T288P and S200N and variant 3: F188L, D261G, abd T288P

| Variant | hardness | moistness | cohesiveness | crumbliness |
| --- | --- | --- | --- | --- |
| Variant 1 | 3.2 | 4.7 | 6.0 | 3.1 |
| Variant 3 | 7.3 | 3.1 | 5.3 | 4.5 |

Example 5: Effect of Variant Maltogenic Alpha-Amylases on the Firmness and Resilience of Small White Bread White breads were baked according to a recipe including 100% flour, 59% regular tap water, 4% yeast, 1.8% salt, 0.3% calcium propionate, and 0.5% basic bread improver (with percentages expressed as baker's percentage, relative to the amount of flour=100%), following the straight dough breadmaking procedure known to a person skilled in the art. MAM variant 3 comprising amino acid substitutions F188L, D261G, T288P and MAM variant 1 comprising F188L, D261G, T288P and S200N were dosed at 8 ppm (0.08 units/g flour). The breadmaking procedure involved a single mixing step after addition of all ingredients to the mixer, followed by fermentation, scaling (at 350 g doughs) and shaping, proofing and baking. The resulting breads were stored at ambient temperatures and evaluated on crumb firmness and resilience.

The results in Table 7 show that the breads prepared with MAM variant 1 comprising F188L, D261G, T288P, and S200N were less firm and exhibited a reduced decrease in resilience than bread prepared with MAM variant 3 comprising F188L, D261G, and T288P after storage at ambient temperature for 0 to 8 days.

TABLE 7

Crumb firmness (g) and resilience (%) of smaller white breads made with MAM variant 3 comprising amino acid substitutions F188L, D261G, T288P and MAM variant 1 comprising F188L, D261G, T288P S200N after storage during several days

| storage time | Firmness (g) | | Resilience (%) | |
| --- | --- | --- | --- | --- |
| (days) | Variant 3 | Variant 1 | Variant 3 | Variant 1 |
| 0 | 149 | 117 | 78.3 | 78.9 |
| 1 | 235 | 207 | 75.9 | 76.1 |
| 4 | 368 | 303 | 72.6 | 73.7 |
| 8 | 386 | 339 | 71.8 | 72.9 |

---

The invention claimed is:

1. A variant polypeptide having maltogenic alpha-amylase activity wherein, the variant polypeptide comprises an amino acid sequence, which, when aligned with an amino acid sequence of SEQ ID NO: 1, comprises amino acid substitutions F188L, S200N, and D261G, and optionally a further amino acid substitution T288P, wherein the amino acid substitutions are determined with reference to SEQ ID NO: 1, and wherein the variant polypeptide has an amino acid sequence which has at least 70%, 75%, 80%, 85%, 90%, 95%, 96%, 97%, 98%, or at least 99% identity to the amino acid sequence of SEQ ID NO: 1.

2. The variant polypeptide according to claim 1, wherein the variant polypeptide has a decreased dependency on calcium ions for thermostability as compared to a reference polypeptide not having the amino acid substitutions F188L, S200N, and D261G, and optionally a further amino acid substitution T288P.

3. The variant polypeptide having maltogenic alpha-amylase activity according to claim 1, wherein the variant polypeptide has at least 40% residual maltogenic alpha-amylase activity after incubating the polypeptide in 50 mM malic acid buffer pH 5.2, containing 50 mM NaCl and 0.05% Bovine Serum Albumin (BSA) and 2 mM Ethylene-diaminetetraacetic acid (EDTA) at a temperature of 87.4° C. for 10 min.

4. A composition comprising a variant polypeptide according to claim 1.

5. A nucleic acid sequence encoding a variant polypeptide according to claim 1.

6. An expression vector comprising a nucleic acid sequence according to claim 5, operably linked to one or more control sequences that direct expression of the nucleic acid sequence.

7. A recombinant host cell comprising a nucleic acid sequence according to claim 5 or an expression vector comprising said nucleic acid sequence.

8. A method for preparation of a variant polypeptide according to claim 1, comprising cultivating a recombinant host cell in a suitable fermentation medium, under conditions that allow expression of the variant polypeptide, and optionally recovering the variant polypeptide.

9. A product comprising a variant polypeptide according to claim 1 for reducing crumb firmness of bread.

10. The product according to claim 9, wherein the bread is white bread or wholemeal bread.

11. A premix comprising flour and a variant polypeptide according to claim 1.

12. A dough comprising a variant polypeptide according to claim 1 or a premix comprising flour and said variant polypeptide.

13. A process for preparation of a dough comprising the variant polypeptide according to claim 1, the process comprising adding said variant polypeptide or a premix comprising flour and said variant polypeptide to a dough.

14. A process for preparation of a baked product comprising baking the dough according to claim 12.

15. A premix comprising flour and the composition according to claim 4.

16. A dough comprising the composition according to claim 4.

17. A dough comprising the premix according to claim 15.

18. A process for preparation of a dough comprising the composition according to claim 4, the process comprising adding said composition to a dough.

19. A process for preparation of a dough comprising the premix according to claim 16, the process comprising adding said premix to a dough.

* * * * *